United States Patent [19]

Dunnigan et al.

[11] 4,057,582
[45] Nov. 8, 1977

[54] AMINOTETRALINS AND USE IN INDUCING ANESTHESIA

[75] Inventors: Daniel Ambrose Dunnigan, Winthrop Harbor; Adolph Oscar Geiszler, Mundelein; James Brooks Holland, Zion, all of Ill.

[73] Assignee: Abbott Laboratories, North Chicago, Ill.

[21] Appl. No.: 401,018

[22] Filed: Sept. 26, 1973

[51] Int. Cl.$^2$ .............................................. C07C 91/16
[52] U.S. Cl. .................................... 260/574; 260/573; 260/501.17; 260/343.7; 424/330
[58] Field of Search .............................. 260/573, 574

[56] References Cited

U.S. PATENT DOCUMENTS

| 2,982,783 | 5/1961 | Schenck et al. | 260/574 X |
| 3,534,055 | 10/1970 | Gittos et al. | 260/574 X |
| 3,637,740 | 1/1972 | Sarges | 260/574 X |

OTHER PUBLICATIONS

Graeff et al., "Chem. Abstracts," vol. 76, abstr. #30552t (1972).

*Primary Examiner*—Elbert L. Roberts

*Attorney, Agent, or Firm*—Gildo E. Fato; Robert L. Niblack

[57] ABSTRACT

Covers a compound selected from the group consisting of a member of the formula:

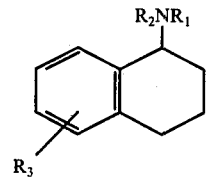

where $R_1$ is a radical selected from the group consisting of higher branched or straight chain alkyl and cycloalkyl radicals wherein said $R_1$ radical contains at least six carbon atoms, $R_2$ is a radical selected from the group consisting of hydrogen, loweralkyl and loweralkanol radicals, wherein said $R_2$ radical contains 1-3 carbon atoms, and $R_3$ is methoxy; and nontoxic pharmaceutically acceptable acid addition salts thereof. Also covers the use of said compound as a local anesthetic and pharmaceutical compositions comprising said above compounds as the active ingredient.

2 Claims, No Drawings

AMINOTETRALINS AND USE IN INDUCING ANESTHESIA

BACKGROUND OF THE INVENTION

Local anesthetics are pharmaceutical materials useful in the relief of many discomforts such as teething, sunburn, pruritus, various dental and surgical procedures, for temporary relief of minor burns, cuts, scratches, nonpoisonous insect bites, poison ivy and other minor skin irritations. They may also be used for postpartum care. In brief, local anesthetics may be employed for diminishing the pain in a restricted area as distinguished from general anesthetics used for eliminating the perception of all stimuli. Many of the known local anesthetics are derivatives of p-aminobenzoic acid; for example, procaine, tetracaine and butacaine. Lidocaine is another type of local anesthetic in wide use.

There is constant interest in developing compounds showing improvement in the therapeutic index over conventional anesthetics such as the above and others. In particular, there is a striving to discover local anesthetics which have a relatively short onset and longer duration of action than those presently employed.

SUMMARY OF THE INVENTION

In summary, we have discovered novel aminotetralin compounds which find particular utility as local anesthetics.

These compounds are selected from the group consisting of a member of the formula:

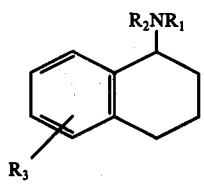

where $R_1$ is a radical selected from the group consisting of higher branched or straight chain alkyl and cycloalkyl radicals wherein said $R_1$ radical contains at least six carbon atoms, $R_2$ is a radical selected from the group consisting of hydrogen, loweralkyl and loweralkanol radicals, wherein said $R_2$ radical contains 1–3 carbon atoms, and $R_3$ is methoxy; and nontoxic pharmaceutically acceptable acid addition salts thereof.

DETAILED DESCRIPTION OF THE INVENTION

In order to prepare the compounds of the invention, it is preferred to begin with various methoxy tetralines such as 6-methoxy-1-tetralone, and 5-methoxy-1-tetralone. These are well known materials whose preparation needs little elaboration.

In order to prepare the compounds here essentially two general methods were followed. In Method I the methoxy tetralones were reacted with long chain alkyl or cycloalkyl amines to produce the substituted ketamines which in turn were hydrogenated to the final amine products.

In Method II the methoxy tetralones were reacted with hydroxyl amine to form the corresponding oximes. The oximes were reacted with hydrogen to form the primary amino compound, which compound in turn was reacted with a long chain alkyl or cycloalkyl aldehyde to form a Schiff base. The Schiff base thus formed was then reduced to form the secondary amine compound containing the long chain alkyl or cycloalkyl radical.

The following examples illustrate preparation of typical compounds of the invention. It is understood, of course, that these examples are merely illustrative, and that the invention is not to be limited thereto.

EXAMPLE I

Here 0.1 mole (17.6 g.) of 5-hydroxy-1-tetralone was reacted with 0.1 mole (11 g.) of N-hexylamine in the presence of 200 ml. benzene solvent. Para-toluene sulfonic acid was employed as a catalyst. The benzene solution was refluxed for about 72 hours until the theoretical amount of 1.8 ml. of water was collected in a water separator. The benzene was then stripped to produce the corresponding N-hexyl ketamine compound.

0.1 Mole of the ketamine in 200 ml. ethanol was then hydrogenated with Raney nickel catalyst (6 g.). After no additional uptake of hydrogen was noted the reaction was stopped. The reaction mixture was filtered, the solvent removed and the product was distilled.

The product has a boiling point of 161° C./1.3 mm. and an index of refraction $N_D^{25}$ 1.5203. The product having a structure as follows:

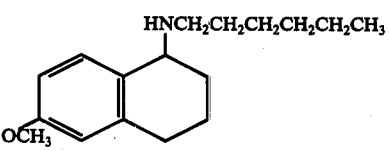

analyzed as follows:

| Element | Theory | Found |
| --- | --- | --- |
| C | 78.11 | 78.51 |
| H | 10.41 | 10.75 |
| N | 5.36 | 4.99 |

EXAMPLE II

Here the procedure of Example I was followed with the exception that N-heptyl amine was employed as a reactant in place of the N-hexyl amine of Example I.

Specifically, 0.1 mole (17.6 g.) of 5-methoxy-1-tetralone was reacted with 0.1 mole (12 g.) of N-heptyl amine in presence of benzene solvent and para-toluene sulfonic acid catalyst. After the theoretical amount of water was split out by azeotropic distillation the corresponding N-heptyl compound was obtained.

The ketamine was then again hydrogenated in presence of Raney nickel catalyst and the reaction was run until hydrogen uptake ceased. The crude product was filtered, washed, solvent stripped and then distilled. The product which had a structure of

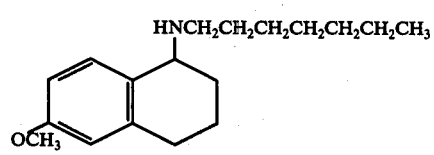

had a boiling point of 171°–74° C./1.2–1.4 mm. and a refractive index of $N_D^{25}$ 1.5182. The product analysis was as follows:

| Element | Theory | Found |
|---------|--------|-------|
| C | 78.49 | 78.23 |
| H | 10.61 | 10.93 |
| N | 5.06 | 4.71 |

Other products may be formed in the same manner as illustrated in the above examples. Table I shows typical additional products falling within the scope of the invention.

Table I

| $R_1$ | $R_2$ | $R_3$ |
|-------|-------|-------|
| —(CH$_2$)$_7$CH$_3$ | H | 6-OCH$_3$ |
| —(CH$_2$)$_8$CH$_3$ | H | 6-OCH$_3$ |
| —(cyclohexyl) | H | 6-OCH$_3$ |
| —(CH$_2$)$_6$CH$_3$ | H | 5-OCH$_3$ |
| —(CH$_2$)$_6$CH$_3$ | CH$_3$ | 6-OCH$_3$ |
| —(CH$_2$)$_6$CH$_3$ | CH$_2$CH$_2$OH | 6-OCH$_3$ |
| —CH(CH$_2$)$_4$CH$_3$<br>   \|<br>   CH$_3$ | H | 6-OCH$_3$ |

The N-substituted aminotetralins can be prepared in the form of their halide salts, for example, as shown above. The free base form of the compounds can then be prepared by reacting the salt with an alkaline reagent, for example, sodium carbonate, sodium hydroxide, aqueous ammonia and other such alkaline reagents commonly employed for converting salts to free bases. The free base can be converted, in turn, to the salt form of the compound by reaction with a pharmaceutically acceptable acid, for example, sulfuric, phosphoric, nitric, hydrochloric, hydriodic, hydrobromic, acetic, tartaric, lactic, malic, fumaric, succinic, ascorbic, pyruvic and the like inorganic and organic acids known to be pharmaceutically acceptable.

The substituted aminotetralins of the present invention can be used as local anesthetic agents in the free base form or in the form of pharmaceutically acceptable acid salts of the free bases. For convenience in administration in aqueous solution, it is preferable to use the salt form of the compounds. The free base form is preferable when it is desired to use the compounds in oleaginous pharmaceutical diluents. The compounds of the present invention can be conveniently administered topically or subcutaneously in the form of ointments, salves, aerosol sprays, solutions and the like. The effective amount of anesthetic agent to be administered will, of course, depend upon many factors such as, for example, the size of the local area to be anesthetized, the length of time anesthesia is desired, the nature of the treatment requiring local anesthesia, the physical condition of the subject undergoing treatment and other such factors. It will be understood that the method of the present invention includes any and all such variations in administering effective amounts of the local anesthetic agents of the present invention as would be apparent to those skilled in the art after reading this specification and is not limited to the illustrative embodiments of the invention specifically described herein.

When administered in the form of solution in a pharmaceutical carrier and used as local anesthetics in therapy, the compounds may be present in widely varying concentrations. Typical solutions may contain from 0.02% up to as high as about 10% by weight. The same type of concentrations may be used in suspension, jelly, ointment or base form.

When solutions of the local anesthetics are made, they may be made isotonic by the addition of i.e. sodium chloride. Further, as is known in the art of local anesthesia, the anesthesia effectiveness may be improved by addition of a vasoconstrictor, such as adrenalin, noradrenalin or octapressin.

If necessary repeated applications of the compounds here at therapeutically effective intervals may be made to obtain a prolonged anesthetic effect.

Typical ointment formulations which may be prepared are the following:

FORMULA A

Using the hydrochloride of the topical anesthetic agent of Example II:

For the preparation of 500 g. of ointment to be used as a topical anesthetic agent, containing 5.0% of the active ingredient: Stir, with heating to 70° C. (mixture A)—

|  | G. |
|---|---|
| Stearic acid | 100 |
| Glycerol monostearate | 20 |
| Sorbitan monopalmitate | 20 |
| Beeswax | 10 |
| Methyl p-hydroxybenzoate | 0.25 |
| Propyl p-hydroxybenzoate | 0.15 |
| Stir, with heating to 70° C. (mixture B)— | |
| Example II Compound | 25.0 |
| Sorbitol 70% | 28.5 |
| Polyoxyethylene sorbitan monopalmitate | 10.0 |
| Water | 286.1 |

Add mixture B to mixture A at 70° C. Stir and cool to room temperature. It is then packaged cold into tubes or jars.

FORMULA B

Using the free base of the topical anesthetic agent of Example II:

For the preparation of 500 g. of ointment to be used as a topical anesthetic agent, containing 5.0% of the active ingredient: Stir, with heating to 70° C. (mixture C)—

|  | G. |
|---|---|
| Stearic acid | 100 |
| Glycerol monostearate | 20 |
| Sorbitan monopalmitate | 20 |
| Beeswax | 10 |
| Methyl p-hydroxybenzoate | 0.25 |
| Propyl p-hydroxybenzoate | 0.15 |
| Example II Compound | 25.0 |
| Stir, with heating to 70° C. (mixture D)— | |
| Water | 286.10 |
| Sobitol 70% | 28.5 |
| Polyoxyethylene sorbitan monopalmitate | 10.0 |

Add mixture D to mixture C at 70° C. Stir and cool to room temperature. It is then packaged cold into tubes or jars.

In order to test the efficacy of the compounds of the invention, the compound of Example II in the form of the methanesulfonic acid salt was tested for its local anesthetic effect.

Specifically 1.3 g. of the salt was prepared in 113 ml. of water and buffered with $NaH_2PO_4$ and $Na_2HPO_4$ to a pH of 6.2-6.4. The concentration of the active ingredient was approximately 1%.

A group of six male albino rabbits weighing between 2.4 and 3.6 kg. was used to determine the activity of the above pharmaceutical composition as a local anesthetic. 0.1 cc of the sample was instilled into the right eye of each of the animals. The contralateral eye was instilled with an equal volume of 1% lidocaine HCl. The corneal reflexes were then tested at 5 minute intervals with a stiff hair. Results were as follows:

Table II

|  | Control | \multicolumn{8}{c}{Corneal Response} |
| --- | --- | --- | --- | --- | --- | --- | --- | --- | --- |
|  |  | 0 | 5 | 10 | 15 | 20 | 25 | 30–55 | 60 minutes |
| Lidocaine HCl | + | + | + | – | – | + | + | + | + |
|  | + | + | – | – | + | + | + | + | + |
|  | + | + | – | – | – | + | + | + | + |
|  | + | + | ± | – | – | + | + | + | + |
|  | + | + | + | – | – | + | + | + | + |
|  | + | + | – | – | – | + | + | + | + |
| Example II Compound | + | ± | ± | – | – | – | – | – | + |
|  | + | + | – | – | – | – | – | – | + |
|  | + | ± | – | – | – | – | – | – | + |
|  | + | ± | – | – | – | – | – | + |  |
|  | + | ± | – | – | – | – | – | – | + |
|  | + | ± | – | – | – | – | – | – | + |

+ = No anesthesia
– = Anesthesia
± = Questionable response

From the above it can be seen that the compound of the instant invention as described in Example II appears to have a shorter onset and a longer duration than the lidocaine HCl compound used as a standard.

Various minor additives can be employed in combination with the N-substituted aminotetralines of the present invention such as, for example, stabilizers, preservatives and the like substances for their desired effects. Thus, preservative agents such as benzyl alcohol and the parabens, for example, methyl p-hydroxybenzoate, which are useful for their preservative effects in prolonging the shelf life of the local anesthetics of this invention can be employed with said anesthetics during their administration.

Numerous adaptations and modifications of the foregoing examples and various other examples will be apparent to the person skilled in the art after reading the foregoing specification and the appended claims without departing from the spirit and scope of the invention. All such further examples, adaptations and modifications are included within the scope of this invention.

We claim:
1. A compound selected from the group consisting of a member of the formula

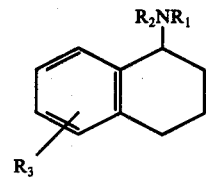

where $R_1$ is selected from the group consisting of a branched or straight chain alkyl of 6–9 carbon atoms and cyclohexyl, $R_2$ is selected from the group consisting of hydrogen, loweralkyl and lower alkanol, wherein said $R_2$ contains 1–3 carbon atoms, and $R_3$ is 5-methoxy or 6-methoxy; and nontoxic pharmaceutically acceptable acid addition salts thereof.

2. The compound of claim 1 which is

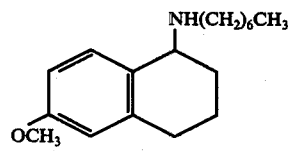

* * * * *